Figure 1:
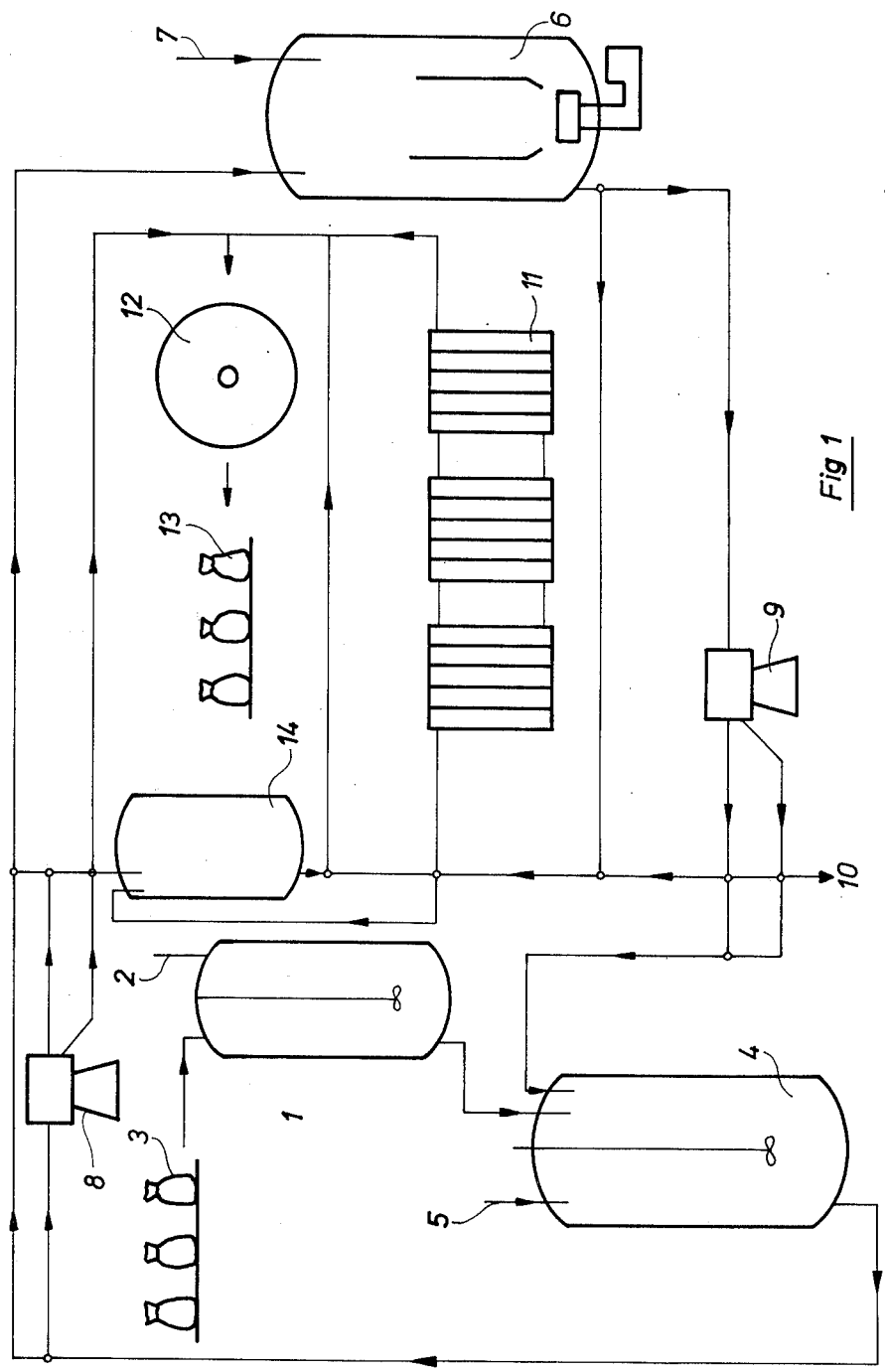

United States Patent [19]

Moebus et al.

[11] 4,327,179

[45] Apr. 27, 1982

[54] METHOD OF BREEDING OF YEAST ON SOLUTIONS, CONTAINING LACTOSE, AND GROUND CEREAL PRODUCTS AND/OR OTHER SUGAR AND POLYSACCHARIDE PRODUCTS

[76] Inventors: Otto Moebus, Lämmerstücken 36, D-2300 Kiel-Russee; Michael Teuber, Gartenstrasse 114, D-2302 Flintbeck; Peter Kiesbye, Zastrowstrasse 16, D-2300 Kiel, all of Fed. Rep. of Germany

[21] Appl. No.: 130,228

[22] Filed: Mar. 14, 1980

Related U.S. Application Data

[63] Continuation of Ser. No. 858,891, Dec. 8, 1971, abandoned.

[30] Foreign Application Priority Data

Dec. 15, 1976 [DE] Fed. Rep. of Germany ....... 2656663
Nov. 24, 1977 [DE] Fed. Rep. of Germany ....... 2752485

[51] Int. Cl.$^3$ ............................................. C12P 39/00
[52] U.S. Cl. ....................................... 435/42; 426/41; 426/42; 426/43; 426/44; 426/49; 426/60; 426/31; 435/255
[58] Field of Search ................... 42/31, 41, 42, 43, 44, 42/49, 60; 435/139, 244, 255, 42

[56] References Cited

U.S. PATENT DOCUMENTS

| | | | |
|---|---|---|---|
| 1,123,920 | 1/1915 | Pollak | 435/139 |
| 1,170,110 | 2/1916 | Roth | 435/255 |
| 1,475,471 | 11/1923 | Corby et al. | 435/255 |
| 1,571,932 | 2/1926 | Corby et al. | 435/255 |
| 1,580,550 | 4/1926 | Wocoten | 435/255 |
| 1,624,674 | 4/1927 | Pollak | 435/139 |
| 1,726,768 | 9/1929 | Robinson | 435/139 |
| 1,784,618 | 12/1930 | Barrington | 435/139 X |
| 3,818,109 | 6/1974 | Bechtle | 426/41 |
| 3,838,006 | 9/1974 | Hijiya et al. | 435/95 |

FOREIGN PATENT DOCUMENTS 2629298 9/1977 Fed. Rep. of Germany ...... 435/244

*Primary Examiner*—Robert J. Warden
*Attorney, Agent, or Firm*—Davis, Hoxie, Faithfull & Hapgood

[57] ABSTRACT

A method of breeding yeast on residual solution containing lactose from dairies, and ground cereals, leguminous products and/or other raw materials, containing sugars and polysaccharides, ammonia being added as the sole inorganic substance.

12 Claims, 1 Drawing Figure

METHOD OF BREEDING OF YEAST ON SOLUTIONS, CONTAINING LACTOSE, AND GROUND CEREAL PRODUCTS AND/OR OTHER SUGAR AND POLYSACCHARIDE PRODUCTS

This is a continuation of application Ser. No. 858,891, filed Dec. 8, 1971, now abandoned.

The present invention relates to a method of breeding of yeast on residual solutions containing lactose from dairies, and ground cereals, leguminous products and/or other raw materials, containing sugars and polysaccharides, ammonia being added as the sole inorganic substance.

Residual solutions, containing lactose, from dairies are difficult to utilize, as large solution volumes with a low solids content must be worked up. A complete utilization can be obtained, if the whey is dried in an untreated state or if yeast, bred on the whey, is dried. In this case no waste water is obtained, if the vapours from the evaporator are not considered.

If yeast is bred on whey (technical processes for the breeding of yeast on whey are reported by L. Forman et al. Kvasny prumysl, 21, 1975, Vol. 12, pages 283–285) a biomass is obtained from a solution of lactose and acids, simple nitrogen compounds like ammonia and ammonium sulphate being added. Thus the protein content of the final product is increased over the untreated material. The ash content of the product obtained by yeast breeding and drying of the total material is too high, as compared with the untreated product. This depends on the loss of weight at the yeast breading (ca 40% of the lactose) and on the sulphuric acid or ammonium sulphate, that has been added to control the pH-value. (The addition of ammonium sulphate is equivalent to the addition of sulphuric acid, as the ammonia from the former is assimilated by the yeast and the sulphuric acid remains in solution). At the termination of the yeast breeding, the acids are neutralized with alkali, which adds to the ash content. It is important to neutralize the acids, because otherwise concentrated acids will arise at the evaporation process. (The concentration ratio is about 500, as 1000 kgs of whey contain 940 kgs of water, and 40 kgs yeast with 4–5% water are obtained. Thus the final product just contains 1.5–2 kgs of the original water content.)

It would be advantageous to add an acid, that is consumed during the yeast breeding step. According to the "Polyvit-process" nitric acid is used, that is utilized simultaneously as a source of nitrogen (B. Waeser, Chemiker Zeitung 7, 1944, pages 120–125). Today it is known, that in the case of oxygen deficiency, nitrite, formed from nitrate, may react spontaneously, or in the presence of microorganisms, with secondary amines to form carcinogenous nitrous amines (J. Sander Hoppe—Seyler's Z. Physiol. Chem. Vol. 349, 1968, pages 429–432). An addition of nitric acid cannot, consequently, be recommended. Lactic acid has proved to be advantageous for the control of the pH-value in aerobic yeast breading with mixed cultures of yeasts and lactic acid bacteria. (O. Moebus and P. Kiesbye, West German OS Specifications No. 24 03 306, 24 10 349.5, 25 003 23.5).

The yeasts assimilate the lactic acid as a source of carbon. Lactic acid bacteria, bred together with the yeasts in a mixed culture, form lactic acid, that is needed for the pH-value control, even under aerobic conditions. Ammonia is added in controlled amounts to the whey and is bound to the lactic acid as ammonium lactate. Together with whey solutions of carbo hydrates, starch or cellulose may generally be used as substrate. In view of the expensive drying operation additional concentrated carbohydrate sources are added to the whey.

L. Forman et al. add ethanol to the whey and achieve a marked rise in the dry solids. Such an addition can only be justified, if cheap, synthetic ethanol is available. If ethanol has to be produced from raw materials, containing starch, it is more convenient to decompose these enzymatically and then use the products obtained together with the whey for the breeding of yeast (H. Müller, West German OS Specification No. 25 48 641, filed Oct. 30, 1975). It would be necessary, however, to test the cultures on the new medium. Until now, yeast strains that assimilate lactose, have been used for the breeding of yeast on whey, such as *Kluyueromyces fragilis* (syn. *Saccharomyces fragilis*) and *Candida kefir* (syn. *Candida pseudotropicalis*). These strains cannot (according to J. Lodder, 1970, North Holland Publishing Company, Amsterdam, Holland), assimilate maltose. The culture yeasts, like *Saccharomyces cerevisiae* are very well adapted to vegetable substrates, containing maltose. It would be convenient for this reason to use mixed cultures of yeasts and lactic acid bacteria with adapted assimilation characteristics for the breeding of yeast on whey in combination with raw material, containing polysaccharides.

It is an object of the present invention to develop an advantageous process of the type mentioned by way of introduction. It is also an object of the present invention to provide a plant for the performance of this process.

According to the present invention there is provided such a method, comprising a first process stage, in which the starch is converted to dextrines, and the lactose is fermented to lactic acid by the action of lactic acid bacteria, that are able to ferment lactose and any other sugars or polysaccharides to acids, ammonia being added, whereupon, in a second process stage the lactic acid suspension so obtained is used for the breeding of yeast, additional ammonia and air being added, the dextrines being hydrolyzed by the action of amylases at the termination of the process in the first stage, or alternatively during the process of the second stage.

In one advantageous embodiment of the present invention, starch is converted to dextrines by the action of thermostable bacteria-a-amylase.

In another advantageous form of the present invention, Yoghourt-bacteria *Lactobacillus bulgaricus* and *Streptococcus thermophilus* are used for the fermentation.

It is preferred to breed *Saccharomyces cerevisia* in the second process stage, but other yeast strains may be used as well.

In one embodiment of the present invention, in which the dextrines are hydrolyzed during the second process stage, the amylases are added continuously in order to prevent, to a great extent, any formation of alcohol.

It is especially advantageous to perform the first process stage at a temperature, higher than 40° C., and to perform the second process stage at a temperature, that is not substantially higher than 32° C. In the first process stage lactic acid is produced by the action of thermophilic lactic bacteria, and the temperature is set on such a high level, that the development of any detrimental microorganisms is prevented, the amylases utilized working at the same time at their temperature optimum. The temperature in the second process stage should be low, to obtain a final product with a high content of yeast protein, and to obtain a high yield of yeast dry solids.

The second process stage of breeding yeast could be performed batchwise. It might be desirable, however, to perform the breeding of yeast as a continuous operation. There are some problems, however, connected to an attempt to perform the yeast breeding on substrates of the type obtained in the first process stage, according to the invention, in a continuous way in a steady state operation. If the rate of dilution, i.e. the ratio of the amount of liquid flow through a fermenter per unit of time to the volume of liquid in the fermenter, is very high, the carbohydrates will preferably be assimilated, whereby the concentration of lactic acid or the lactate will rise in the culture. Finally, this concentration will become inhibiting to the yeast growth.

To overcome this disadvantage, the second process stage of the present invention is performed in a special semicontinuous way. Thus the breeding of the yeast takes place in two distinct, repeated phases, phase I with a duration of time $\Delta t_1$ and phase II with a duration of time $\Delta t_2$, suspension from the first process stage, containing lactice acid, ammonium lactate and carbo hydrates as sources for C and N being fed to a fermenter during the time $\Delta t_1$ in an amount of $\Delta g$. In phase II no further suspension is added, til the lactic acid, that has accumulated in the culture solution during the time $\Delta t_1$ has been assimilated. At the end of phase II (after a period of time = $\Delta t_2$) an amount of yeast suspension of weight $\Delta g$ is withdrawn from the fermenter. The ratio of $\Delta g/\Delta t_1$ is chosen in such a way, that $\Delta t_2 > 0$.

The suspension may be fed, during phase I, in a steady flow, or adapted to the yeast growth, e.g. according to a logarithmic pattern.

There are many ways of controlling the feed of suspension, such as measurement of the alcohol content in the fermenter, or by measuring the end point of the consumption of nutrition in phase II by means of an oxygen electrode, or carbondioxide electrode. The end point can as well be estimated by measurement of the paramagnetic characteristics of residual oxygen in the exhaust gas, or by measurement of the infrared absorption of carbon dioxide in the exhaust gas. Further, the end point can be determined by measurement of the heat of reaction in the fermenter.

The process according to the invention is quite advantageous, as the addition of raw material, containing starch, to the whey or other residual solutions with a lactose content, and performing the process, gives rise to final product with a reasonable ash content. There is practically no waste water. The product obtained may be used as a valuable protein and vitamin source for feed. If culture yeasts are bred, the products may be used as food, as there are no toxicological obstacles for this.

The process according to the invention may be adapted to any available raw materials. Apparatus for the performance of the process may be varied in many ways in view of the desired final product.

Further features and advantages of the process and the apparatus for carrying out the process will appear from the following description of two preferred embodiments thereof with reference to the accompanying FIGURE, which is a schematic representation of a first embodiment of apparatus for carrying out the process according to the invention.

The apparatus shown may be used in a variety of ways. The apparatus comprises a tank 1 provided with heating and cooling means, an inlet 2 for the lactose solution and an inlet 3 for starch containing raw materials, and a tank 4, provided with an inlet 5 for ammonia, and means for temperature control. Tank 1 is used for gelatinization and converting of starch into dextrine, whereas tank 4 is intended for the lactic acid fermentation. The dextrine hydrolysis may be carried out in this tank 4, too. Thus tank 1 and 4 are used for the first process stage of the invention. Further the apparatus comprises a tank 6 for the yeast breeding, which tank 6 is provided with an ammonia inlet 7. Thus tank 6 is used for the second process stage of the invention. The apparatus comprises further items, that may be used according to the desired mode of operation.

Thus there are provided centrifugal separators 8 and 9 for the separation of solids and lactic acid bacteria, and for preconcentration of yeast suspension 10 from tank 6. Both separators are preferably of the selfemptying type. Also, there are means for the production of a dry final product, like an evaporator 11, a spray drier 12 and a bagging plant 13. An intermediate cooled tank 14 is provided for the storage of fermented suspensions, yeast suspensions, centrifugal separation residues and centrifugates. The different items are connected to each other according to the lines drawn in the FIGURE.

EXAMPLE 1

In this example apparatus as shown in FIG. 1 was used. 4000 kgs of wheatflour (63.3% starch, 13.3% raw protein/Kjeldahl-N×6.25/1.6% ashes and 11.6% water) were mixed at low temperature with 20,000 kgs of whey. An amount of thermostable bacteria-a-amylase (e.g. 900 mls Termamyl 60 L NOVO) sufficient for the conversion of starch into dextrines was added, and the mixture was heated to 75° C. by steam. (Gelatinization starts at about 65° C., but the action of amylase makes the suspension less viscous). The suspension was kept at 70°–80° C. for 30 minutes, and was then cooled to 50° C., whereupon 80 liters of yoghourt culture was added. The pH-value was adjusted to 6.2 by addition of 25% aqueous ammonia and kept at 6.2 till 200 liters of 25% ammonia solution were consumed. After 10 hours of fermentation at 50° C. a pH-value of 4.3 was achieved, that did not change noticeably after that. For the hydrolysis of the dextrines a fungal amylase (such as 500 mls of Fungamyl 800 L NOVO) is added. This can be done at the end of the lactic acid fermentation. It may also be convenient, however, to add the amylase during the yeast breeding, as the speed of reaction is sufficient even at the lower temperature prevailing at this stage. In this case the maltose formation may be controlled, to minimize the alcohol formation.

EXAMPLE 2

In this example the yeast breeding was performed in a semicontinuous way. A suspension from the first process stage of the invention was obtained with the following composition:
Lactid acid-D: 15.5 g/l
Lactic acid-L: 16.6 g/l
Ammonia: 4.5 g/l
Carbohydrates: 127 g/l (in the form of enzymatically decomposed starch).

The yeast breeding was performed in an aerated fermenter. In table 1 one phase I with continuous feed of substrate and one phase II without any feed are shown. *Saccharomyces cerevisia* was used.

From the table it is obvious, that lactic acid-C as well as lactic acid-L rise in concentration during phase I. The D-isomer of lactic acid is assimilated by the yeast at a higher rate than the L-form. After the $O_2$-partial pressure has risen in the culture, i.e. at the end of phase II, both isomers of lactic acid are practically completely assimilated by the yeast.

TABLE 1

Yeast breeding on a substrate, obtained from whey + 20% wheat-flour, by lactic acid fermentation and amylase-treatment, Temperature = 23° C.

| Time hours | $O_2$-pressure % saturation | Lactic acid D g/l (cell-free solution) | Lactic acid L g/l (cell-free solution) | pH | $NH_3$ g/l | COD ($KMnO_4$) mg $O_2$/l (cell-free solution) | |
|---|---|---|---|---|---|---|---|
| 0.00 | | | | | | | Start of feed |
| 0.50 | 55 | 0.43 | 0.67 | 4.8 | 0.39 | 320 | |
| 1.50 | 15 | 0.77 | 1.21 | 4.8 | 0.54 | 2240 | |
| 2.50 | 4 | 1.14 | 2.29 | 5.0 | 0.85 | 5120 | |
| 3.50 | 3 | 1.57 | 3.54 | 5.1 | 1.05 | 5540 | End of feed |
| 4.50 | 1 | 0.87 | 2.03 | 5.5 | 0.80 | 5120 | |
| 6.50 | 1 | 0.17 | 0.15 | 6.0 | 0.37 | 4000 | |
| 8.00 | 1 | — | — | 5.7 | — | — | |
| 8.75 | 55 | 0.07 | 0.12 | 5.8 | 0.25 | 1920 | Recovery of yeast |

$\Delta g$ = 3 kgs
$\Delta t_1$ = 3.50 hours
$\Delta t_2$ = 5.25 hours
Yeast growth/3 kgs substrate solution: 364 grams of yeast dry solids, corr. to 1162 moist yeast substance.

We claim:

1. A process for producing yeast from dairy liquids containing lactose and natural materials containing sugars and polysaccharides, comprising in combination the steps of:
   a. preparing a mixture of the lactose containing dairy liquid and the natural materials containing sugars and polysaccharides, an amylase of the type that converts starch into dextrine, and lactic acid bacteria;
   b. fermenting the lactose into lactic acid and converting the sugars and polysaccharides to dextrines, ammonia being added during this conversion to control the pH of the mixture;
   c. subsequent to the lactose conversion step, adding amylase to hydrolyze the dextrines; and
   d. either concomitant with or subsequent to the dextrine hydrolysis, adding a yeast to the suspension resulting from the lactose and sugar-polysaccharide and fermenting the mass under aerobic conditions, controlling the pH by addition of ammonia;
   e. and further wherein the yeast fermentation step (d.) is conducted semicontinuously in two distinct repeated phases, as follows:
      (i) an amount, $\Delta g$, of suspension from the lactose and starch conversion step comprising lactic acid, ammonium lactate and carbohydrates as sources for carbon and nitrogen is flowed to a fermentor during a time period $\Delta t_1$, the lactic acid concentration increasing during $\Delta t_1$ to a predetermined level;
      (ii) after the lactic acid has reached said predetermined level, the flow of suspension from the lactose and starch conversion step is terminated for a time period $\Delta t_2$ to permit the lactic acid accumulated during the time period $\Delta t_1$ to become assimilated;
      (iii) at the termination of $\Delta t_2$, an amount of yeast suspension equal in weight to the suspension from the lactose and starch conversion step, $\Delta g$, is withdrawn;
      (iv) thereafter the process steps (1)–(iii) are repeated.

2. The process of claim 1, wherein the diary liquid is whey and the natural materials are selected from the group consisting of ground cereals and leguminous products.

3. The process of claim 2, wherein the starch to dextrine amylase is a thermostable bacteria alpha-amylase.

4. The process of claim 1, wherein the dextrine hydrolysis and yeast cultivation are carried out simultaneously.

5. The process of claim 4, and further wherein the dairy liquid is whey and the natural materials are selected from the group consisting of ground cereals and leguminous products.

6. The process of claim 5, wherein the starch to dextrine amylase is a thermostable bacteria alpha-amylase.

7. The process of claim 4, wherein the starch to dextrine amylase is a thermostable bacteria alpha-amylase.

8. The process of claim 1, wherein the starch to dextrine amylase is a thermostable bacteria alpha-amylase.

9. The process of claim 8, wherein the lactic acid bacteria is yogurt bacteria *Lactobacillus bulgaricus* and *Streptococcus thermophilus*.

10. The process of claim 9, and further wherein the cultivated yeast is *Saccharomyces cerevisiae*.

11. The process of claim 1, wherein the amylase capable of dextrine hydrolysis is added continuously throughout the yeast cultivation step to inhibit the formation of ethyl alcohol.

12. The process of claim 1, wherein the lactose conversion step is conducted at a temperature greater than 40° C. and the yeast cultivation step is conducted at a temperature not substantially higher than 32° C.

* * * * *

UNITED STATES PATENT AND TRADEMARK OFFICE
CERTIFICATE OF CORRECTION

PATENT NO. : 4,327,179
DATED : April 27, 1982
INVENTOR(S) : Otto Moebus, Michael Teuber and Peter Kiesbye It is certified that error appears in the above-identified patent and that said Letters Patent are hereby corrected as shown below:

On the title page

Under "Related U. S. Application Data" -

"1971" should be -- 1977 --

Column 2, line 18    -  "kluyueromyces" should be
                         -- kluyveromyces --

Column 3, line 24    -  "lactice" should be -- lactic --

Column 5, Under "Table 1" -
    After "amylase-treatment" the comma [,] should be a period [.]

Signed and Sealed this

Twenty-second Day of May 1984

[SEAL]

Attest:

GERALD J. MOSSINGHOFF

Attesting Officer    Commissioner of Patents and Trademarks